United States Patent [19]

Hinch et al.

[11] Patent Number: 4,710,946
[45] Date of Patent: Dec. 1, 1987

[54] METHOD AND APPARATUS FOR X-RAY VIDEO FLUOROSCOPIC ANALYSIS OF ROCK SAMPLES

[75] Inventors: Henry H. Hinch, Tulsa; Gail E. Boyne, Sapulpa; David L. Daniels, Haskell; Eugene V. Kullmann, Tulsa, all of Okla.

[73] Assignee: Amoco Corporation, Chicago, Ill.

[21] Appl. No.: 763,100

[22] Filed: Aug. 6, 1985

[51] Int. Cl.[4] .................... G01N 23/08; G01N 23/18; G01V 9/00
[52] U.S. Cl. ........................................ 378/62; 73/153; 250/255; 378/57; 378/58; 378/99; 378/165; 378/208
[58] Field of Search .................... 378/62, 99, 57, 190, 378/208, 45, 5, 165, 10, 61, 60, 59, 58, ; 73/153; 250/255; 358/111

[56] References Cited

U.S. PATENT DOCUMENTS

| 587,883 | 8/1897 | Thomson | 378/190 |
|---|---|---|---|
| 2,462,018 | 2/1949 | Wood | 378/165 |
| 3,373,440 | 3/1968 | Jenkins et al. | 73/153 |
| 3,848,130 | 11/1974 | Macovski | 378/5 |
| 4,029,963 | 6/1977 | Alvarez et al. | 378/5 |
| 4,076,984 | 2/1978 | Gromov et al. | 378/99 |
| 4,472,822 | 9/1984 | Swift | 378/10 |
| 4,540,882 | 9/1985 | Vinegar et al. | 250/255 |
| 4,671,102 | 6/1987 | Vinegar et al. | 73/61.1 |

FOREIGN PATENT DOCUMENTS

| WO83/01509 | 4/1983 | PCT Int'l Appl. . |
| 1569415 | 3/1976 | United Kingdom . |
| 1547371 | 6/1979 | United Kingdom . |
| 2039363 | 8/1980 | United Kingdom . |
| 2073884 | 4/1981 | United Kingdom . |
| 2110037 | 7/1982 | United Kingdom . |

OTHER PUBLICATIONS

Jackson et al, "Real-Time X-Ray Inspection System for Fast Flux Test Facility Fuel," Material Evaluation, vol. 31, No. 10, Oct. 1973, pp. 199-204.

Primary Examiner—Craig E. Church
Assistant Examiner—T. N. Grigsby

[57] ABSTRACT

Method and apparatus involving the use of an X-ray video fluoroscope for nondestructive analysis of rock samples, including core obtained during the drilling of wellbores through subterranean strata, to determine the presence, location, and orientation of any internal features, or to monitor the flow of fluids through the rock sample. Rock samples can be both moved through and rotated in the analysis zone of the X-ray video fluoroscope and the visible light image obtained from the X-ray video fluoroscope can then be viewed, recorded photographically or on video tape, or digitized to facilitate computer implemented storage, retrieval, and digital processing of the X-ray video fluoroscope image.

11 Claims, 1 Drawing Figure

METHOD AND APPARATUS FOR X-RAY VIDEO FLUOROSCOPIC ANALYSIS OF ROCK SAMPLES

BACKGROUND OF THE INVENTION

This invention is related to a method and apparatus for analysis of rock samples, and more particularly, core obtained during the drilling of a wellbore through subterranean strata, with an X-ray video fluoroscope.

In the exploration for and production of minerals and hydrocarbons from the earth's surface and subsurface, it is common practice to obtain rock samples from the subterranean strata or formations of interest. These rock samples are usually obtained from outcroppings of the subterranean strata or from wellbores drilled through the overlaying strata to the subterranean strata of interest. These rock samples are normally analyzed through visual inspection for internal features, such as bedding laminations, fractures, and localized mineralization. However, this type of analysis often requires that the rock sample be cut up, thus resulting in destruction of the particular rock sample.

More particularly, in the drilling of wellbores for the exploration for and production of hydrocarbons from subsurface formations, it is common practice to obtain rock samples in the form of core cut through some of the subterranean formations through which the wellbore is drilled. This core is cut and retrieved in sections of varying length. This core is normally analyzed, through visual petrologic and sedimentologic evaluations and determinations of bedding laminations, fractures and localized mineralization, to provide important information related to depositional environment, structural history, or diagenetic processes. However, since these types of geological evaluations commonly require that the core be slabbed, such evaluations have either been delayed in the past until after production testing, such as fluid flow studies in sections of the core, or core analysis, requiring whole core have been completed, or have not been performed, in cases where there is a need to keep the core sealed or where production testing or core analysis has virtually destroyed the core.

Accordingly, there is a need for a method of and apparatus for nondestructive analysis of rock samples and, more particularly, core obtained during the drilling of a wellbore through subterranean strata to determine the presence of and evaluate such internal features as bedding, laminations, fractures, and localized mineralization.

BRIEF DESCRIPTION OF THE INVENTION

In the present invention, the general object of providing a method of and apparatus for nondestructive analysis of a rock sample for the determination of the presence of and further evaluation of internal features of the rock sample is obtained by placing the rock sample in an X-ray video fluoroscope. A rock sample, such as core obtained during the drilling of a wellbore through subterranean strata, is placed in an X-ray video fluoroscope and preferably is rotated in and moved through the analysis zone of the X-ray video fluoroscope, i.e., that portion of the X-ray video fluoroscope where the rock sample is exposed to the X-ray beam, while X-rays are directed through it, in such a manner so as to completely image any internal features of the particular rock sample, such as bedding laminations, fractures, and localized mineralization. Also, this nondestructive analysis of a rock sample using an X-ray video fluoroscope can be used to monitor the flow of fluids through sections of the rock sample during fluid flow testing conducted on the rock sample. Once again, the rock sample may be both moved through and rotated in the analysis zone of the X-ray video fluoroscope, i.e., that portion of the X-ray video fluoroscope where the rock sample is exposed to the X-ray beam, in order to monitor this flow of fluids through sections of the rock sample. A video image is obtained from the X-ray video fluoroscope, which can then be viewed, recorded photographically or on video tape, or digitized, quantitatively analyzed, or electronically stored in a digital storage means, such as a disk, prior to any further digital analysis.

DETAILED DESCRIPTION OF THE INVENTION

Figure 1:
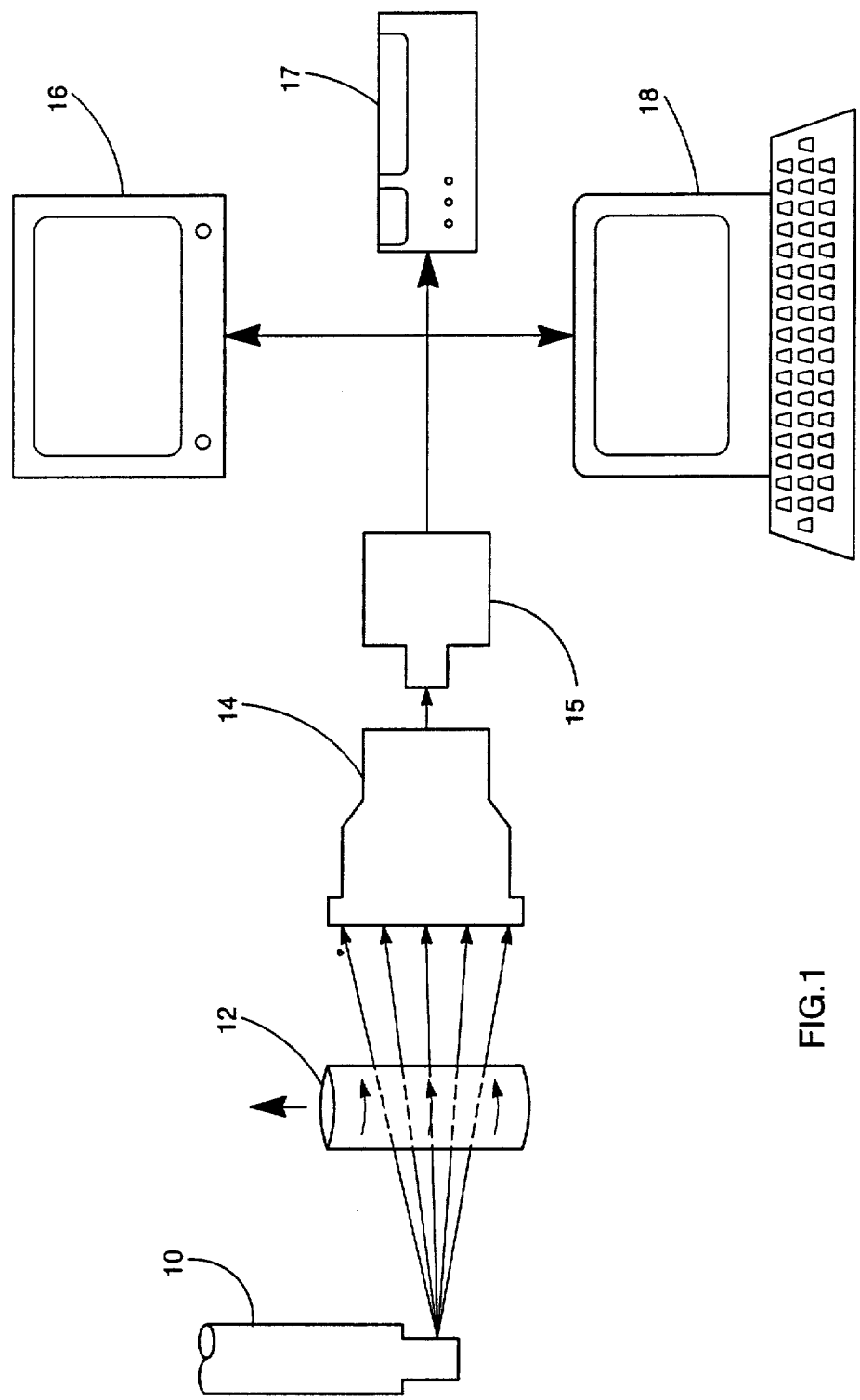
FIG. 1 is a schematic view of a section of core in an X-ray video fluoroscope, in the practice of the present invention.

Briefly, the practice of the present invention involves a method of and apparatus for directing X-rays in an X-ray video fluoroscope through a rock sample and preferably rotating and moving the rock sample in such a manner so as to completely image any internal features of the particular rock sample.

One embodiment of this invention as shown in FIG. 1, involves generating X-rays with sufficient amperage and voltage to image internal features of a particular rock sample with a commercially available X-ray tube 10, passing these X-rays through the rock sample, here a section of core 12, in the analysis zone of the X-ray video fluoroscope, and then passing these X-rays into an imaging device 14, which converts the X-ray image formed as X-rays pass through the core into a visible light image. The visible light image is then picked up by a video camera 15 and displayed on a video monitor 16 as an image that can be viewed by the human eye, recorded photographically or on video tape, or digitized, utilizing a microprocessor 18, so as to facilitate computer aided storage, retrieval, and digital processing and analysis of the image.

Usually, the section of core 12 is rotated in and moved through the analysis zone of an X-ray video fluoroscope as the X-rays pass through it, in order to determine the presence, location, identification, and orientation of any X-ray determinable internal features of the section of core 12. From this examination of the section of core 12, either an interpretative depositional environment log or an interpretative log of the fracture morphology and spacing within the subterranean formations through which the core 12 was obtained can be made. Also, determinations can be made of the amount of core recovered, the quality of core recovered, and locations down the length of the core from which core plug samples should be obtained for further production testing or core analysis. The section of core 12 can also be rotated, if necessary, and moved through the analysis zone as the X-rays pass through it, in order to monitor the fluid flow characteristics through the section of core 12 during fluid flow testing conducted on the section of core 12. In conducting this fluid flow testing, fluids containing an X-ray absorber such as potassium iodide or iodobenzene are flowed through the section of core 12. The flow of these fluids through the section of core 12 can then be monitored with the X-ray video fluoroscope and the fluid flow characteristics of the section of core 12 can be determined.

In one embodiment of the invention, the section of core 12 is moved through and continuously rotated in the analysis zone of the X-ray video fluoroscope such that a site on the exterior surface of the core is rotated through at least 360° during the time in which this site is within the X-ray video fluoroscope analysis zone, i.e., that area of the X-ray video fluoroscope where X-ray beams pass through the core. This particular combination of movement and rotation is advantageous in order to provide a complete check of the section of core 12 while it is within the analysis zone of the X-ray video fluoroscope, for the presence of any X-ray determinable internal features. In another embodiment of this invention, the core is marked in such a way that there is provided on the X-ray video fluoroscope image a marking of orientation of the core within the core barrel when it was cut, and depth location of the core in the wellbore, and dimensions on or within the core, from which both the orientation and depth location of any part of the core or any internal features of the core can be determined and from which the dimensions of any internal features can be determined.

It is thought that internal features of the core are observed with an X-ray video fluoroscope because of differential spatial attenuation of the X-ray beam as it passes through the core. The amount of X-ray attenuation increases with (1) a decrease in core porosity, (2) an increase in average core bulk density, (3) a transition within the core from low X-ray attenuation mineral constituents (e.g., quartz or feldspar) to high X-ray attenuation mineral constituents (e.g., calcite, chlorite, pyrite), and (4) variations in the core pore fluid composition such that the average X-ray attenuation of the pore fluid increases. If all of these parameters were uniform throughout the core, then uniform spatial attenuation of the X-ray beam could occur, resulting in no image or more specifically, a uniform gray level image of the core. If any or all of these parameters vary spatially to the extent that there is a resulting detectable spatial variation in X-ray attenuation as the X-ray beam passes through the core, then an X-ray image will be formed wherein the high X-ray attenuation areas appear dark and the low X-ray attenuation areas appear light. In nature, porosity, bulk density, mineralogy, and pore fluid compositions are never constant. They do, however, vary spatially in response to the processes involved in deposition, diagenesis, fluid migration, and mechanical deformation that produced the physical characteristics of the internal features of the rock in question. The spatial variations in these properties occur in such a way that the overall morphological character of the variations is recognizable fluoroscopically as internal features, such as bedding laminae, fractures, localized mineralizations, or fluid distributions.

The use of this technique is illustrated by X-ray video fluoroscope examination conducted on sections of Nugget Sandstone Formation whole core, totalling roughly 150 feet in length. Nugget Sandstone Formation is a cross-bedded Eolian sandstone which exhibits both large scale and small scale bedding features and fractures which result in lateral and vertical heterogeneity with respect to porosity and permeability.

This X-ray video fluoroscope examination was conducted using X-rays in the range of 18 to 159 KVP (kilovolt potential) at 1 to 30 ma (milliamps), generated with a commercially available TFI Gemini II industrial X-ray tube. After having passed through the core, the X-rays were converted into a visible light image using a commercially available Macklett Dynavision image intensifier system.

In order to hold, manipulate, and view core in the X-ray video fluoroscope, the core was placed in a core holder which consisted of a 6 ft length of 4½ in. diameter aluminum pipe, which had been cut into equal halves along its length. Sections of whole core were placed within the core holder and the two pieces of the core holder were mated and secured to one another. Initially, the principal orientation scribe on each piece of core (which provides an indication of orientation of the core within the core barrel when it was cut and from which the orientation of the core in the wellbore can be determined) was juxtapositioned against one of the resulting seams of the core holder. When viewed on the X-ray video fluoroscope monitor, the seam where the halves of the core holder came together showed up as a vertical white line, providing an indication of the location of the principal orientation scribe on the X-ray video fluoroscope image of the core, which in turn provides a means for determining the orientation in the core barrel, and hence the wellbore, of both the core and any internal features of the core. Later, a linear, X-ray absorptive, metal marker, which was affixed to the exterior of the core holder so as to be juxtapositioned against the principal orientation scribe and which showed up as a vertical black line on the X-ray video fluoroscope image, was used to provide an indication of the location of the principal orientation scribe on the X-ray video fluoroscope image of the core.

Because of differences in diameter between the core and the interior wall of the core holder, pieces of foam padding were inserted between the core and the interior wall of the core holder. This prevented the core from changing orientation during rotation. Lead numerals denoting the depth in the wellbore from which the core was obtained were attached at respective lengths along the sample holder with lead arrows indicating the up position, to provide an indication of core depth and depth location of any internal features of the core, as seen on the image of the core on the X-ray video fluoroscope monitor. Individual lead shot spheres were affixed to the core along the principal orientation scribe with 1" or 0.1' spacing to further provide an indication of core depth and depth location of any internal features of the core on the X-ray video fluoroscope image and to provide an indication of the dimensions of these internal features. Where spaces occurred between the butt ends of sections of core inside the core holder, lead strips were fastened to the holder or in front of the holder over these spaces to prevent the X-ray beam from passing directly through these spaces onto the X-ray video fluoroscope image, thereby reducing the quality of the image or causing a whiteout of the entire image. Further, the X-ray beam was masked using lead panels located between the X-ray source and the core, so as to prevent X-rays from passing above and/or below the core inside the core holder, thereby preventing a reduction in the quality of the image or causing whiteout of the entire X-ray video fluoroscope image. The core holder was then placed within a cradle on a conveyor belt running through the analysis zone of the X-ray video fluoroscope, with one end of the core holder attached to a cam driven by an electric motor. This allowed the core holder to be rotated as it was moved through the X-ray video fluoroscope. The speed of movement (roughly 3 ft/min) and rotation (roughly 4 RPM) were controlled by the X-ray video fluoroscope operator. The X-ray video fluoroscope image of the core was viewed on the X-ray video fluoroscope monitor and a video tape was made for future reference. Bedding and fractures were visible on the X-ray video fluoroscope monitor when the strike of the bedding planes or fractures was orientated parallel to the direction of the X-ray beam. In this orientation, the operator was able to measure approximate dip angle directly off the X-ray video fluoroscope monitor with a protractor. The X-ray video fluoroscope image was also digitized and both strike and dip of internal bedding planes or fractures were measured quantitatively utilizing a microprocessor and specially designed image analysis software.

It was found that a rotation of the core by as little as one or two degrees could cause an image of an internal feature in the core to disaphat a rotation of the core by as little as one or two degrees could cause an image of an internal feature in the core to disappear from the output image from the X-ray video fluoroscope. Therefore, in order to provide a complete check for internal features in a core, an output image must be obtained from the X-ray video fluoroscope for at most every one degree of rotation. Because of this and the fact that a video image is made up of a series of individual "frames" shown every second, the speed of rotation, in the case where a video output image from the X-ray video fluoroscope is obtained, must be such that each of the "frames" shown per second contains an image of the core wherein the core has been rotated by at most one degree from the position of the core in the previous "frame".

Fluid flow characteristics of a core were determined by monitoring the flow of fluids containing an X-ray absorber, such as potassium iodide for aqueous phase fluid flow studies and iodobenzene for oil phase fluid flow studies, as these fluids were flowed through core. Because of differential spatial attenuation of the X-ray beam in X-ray absorber containing fluid saturated zones of the core, the distribution of this X-ray absorber containing fluid through the rock sample can be monitored with an X-ray video fluoroscope.

While certain embodiments of the invention have been described for illustrative purposes, the invention is not limited thereto and various other modifications or embodiments of the invention will be apparent to those skilled in the art in view of this disclosure since modifications or embodiments are within the spirit and scope of the disclosure.

What is claimed is:

1. A method for nondestructive analysis of rock samples using an X-ray video fluoroscope comprising the steps of:
    placing a rock sample which has at least one X-ray determinable internal feature in the direction of its major axis in an analysis zone of an X-ray video fluoroscope;
    directing an X-ray beam generated by said X-ray video fluoroscope through said rock sample;
    moving said rock sample in said analysis zone by both moving said rock sample through said analysis zone and simultaneously, continuously rotating said rock sample within said analysis zone around its major axis;
    generating a two-dimensional X-ray image of said internal feature of said rock sample;
    converting said two-dimensional X-ray image into a two-dimensional light image of said internal feature; and
    televising said two-dimensional light image and displaying it on a video monitor such that said internal feature may be seen as it moves through said analysis zone while rotating.

2. A method for nondestructive analysis of rock samples using an X-ray video fluoroscope as recited in claim 1 wherein said continuously rotating said rock sample is such that an output image is obtained from said X-ray video fluoroscope for at most every one degree of rotation of said rock sample.

3. A method for nondestructive analysis of rock samples using an X-ray video fluoroscope as recited in claim 1, wherein a site on the exterior surface of said rock sample is rotated through at least 360° during the time in which said site is within said analysis zone of said X-ray video fluoroscope.

4. A method for nondestructive analysis of rock samples using an X-ray video fluoroscope as recited in claim 1, where an output image obtained from said X-ray video fluoroscope is recorded.

5. A method for nondestructive analysis of rock samples using an X-ray video fluoroscope as recited in claim 1, wherein an output image obtained from said X-ray video fluoroscope is digitized.

6. A method for nondestructive analysis of rock samples using an X-ray video fluoroscope as recited in claim 1, wherein said rock sample comprises core taken during the drilling of a wellbore through subterranean strata.

7. A method for nondestructive analysis of rock samples using an X-ray video fluoroscope as recited in claim 6, further comprising the step of marking said core so as to provide a marking on an output image obtained from said X-ray video fluoroscope of both the orientation and location of said core in said wellbore and the orientation, location, and dimensions, of any internal features of said core.

8. Apparatus for nondestructive analysis of rock samples using an X-ray video fluoroscope to determine the presence of X-ray determinable internal features comprising:
    means for moving a rock sample which has at least one X-ray determinable internal feature in the direction of its major axis through an analysis zone of an X-ray video fluoroscope;
    means for continuously rotating said rock sample around its major axis simultaneously with the moving of said rock sample; and
    means for directing an X-ray beam generated by said X-ray video fluoroscope through said rock sample;
    means for producing a two-dimensional X-ray image of said internal feature of said rock sample;
    means for converting said two-dimensional X-ray image into a two-dimensional light image of said internal feature; and
    means for televising said two-dimensional light image and displaying it on a video monitor such that said internal feature may be seen as it rotates and moves through said analysis zone.

9. Apparatus as recited in claim 8, further comprising means for recording an output image obtained from said X-ray video fluoroscope.

10. Apparatus as recited in claim 8, further comprising means for digitizing an output image from said X-ray video fluoroscope.

11. Apparatus as recited in claim 8, wherein said means for continuously rotating said rock sample is such that an output image is obtained from said X-ray video fluoroscope for at most every one degree of rotation of said rock sample.

* * * * *

UNITED STATES PATENT OFFICE
CERTIFICATE OF CORRECTION

PATENT NO. : 4,710,946

DATED : December 1, 1987

INVENTOR(S) : Henry H. Hinch et al.

It is certified that error appears in the above-identified patent and that said Letters Patent are hereby corrected as shown below:

Column 5, lines 20-22, delete "disaphat a rotation of the core by as little as one or two degrees could cause an image of an internal feature in the core to"

Signed and Sealed this

Fifth Day of July, 1988

Attest:

DONALD J. QUIGG

*Attesting Officer*   *Commissioner of Patents and Trademarks*